US008889373B2

(12) United States Patent
Clendennen

(10) Patent No.: US 8,889,373 B2
(45) Date of Patent: Nov. 18, 2014

(54) ENZYME CATALYST IMMOBILIZED ON POROUS FLUOROPOLYMER SUPPORT

(75) Inventor: Stephanie Kay Clendennen, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 326 days.

(21) Appl. No.: 12/855,117

(22) Filed: Aug. 12, 2010

(65) Prior Publication Data

US 2012/0040395 A1    Feb. 16, 2012

(51) Int. Cl.
*C12P 37/06*    (2006.01)
*C12Q 1/00*    (2006.01)
*C12N 11/08*    (2006.01)
*C12N 11/04*    (2006.01)

(52) U.S. Cl.
CPC ............... *C12N 11/08* (2013.01); *C12N 11/04* (2013.01)
USPC ................................. 435/44; 435/4

(58) Field of Classification Search
None
See application file for complete search history.

(56) References Cited

U.S. PATENT DOCUMENTS

| | | | |
|---|---|---|---|
| 4,051,011 A * | 9/1977 | Miyauchi et al. ............. 204/600 |
| 4,551,482 A | 11/1985 | Tschang et al. | |
| 4,619,897 A | 10/1986 | Hato et al. | |
| 4,629,742 A | 12/1986 | Brady et al. | |
| 4,885,250 A | 12/1989 | Eveleigh et al. | |
| 4,886,836 A | 12/1989 | Gsell et al. | |
| 4,894,339 A | 1/1990 | Hanazato et al. | |
| 4,897,352 A | 1/1990 | Chonde et al. | |
| 4,954,444 A | 9/1990 | Eveleigh et al. | |
| 4,963,494 A | 10/1990 | Hibino et al. | |
| 4,968,605 A | 11/1990 | Hayman | |
| 4,975,375 A | 12/1990 | Haruta et al. | |
| 5,010,006 A | 4/1991 | Ergan et al. | |
| 5,079,155 A | 1/1992 | Cox et al. | |
| 5,128,251 A | 7/1992 | Yokomichi et al. | |
| 5,156,963 A | 10/1992 | Eigtved | |
| 5,182,201 A | 1/1993 | Tsuda | |
| 5,270,193 A | 12/1993 | Eveleigh | |
| 5,279,948 A | 1/1994 | Pedersen et al. | |
| 5,342,772 A | 8/1994 | Arenzen et al. | |
| 5,356,757 A | 10/1994 | Shionoya et al. | |
| 5,384,254 A | 1/1995 | Arentzen et al. | |
| 5,405,618 A | 4/1995 | Buttery et al. | |
| 5,491,083 A | 2/1996 | Arentzen et al. | |
| 5,683,916 A | 11/1997 | Goffe et al. | |
| 5,766,473 A | 6/1998 | Strobel et al. | |
| 5,897,955 A | 4/1999 | Drumheller | |
| 5,914,182 A | 6/1999 | Drumheller | |
| 5,964,993 A | 10/1999 | Blubaugh, Jr. et al. | |
| 5,976,527 A | 11/1999 | Siol et al. | |
| 6,017,742 A | 1/2000 | Takenishi et al. | |
| 6,759,220 B1 | 7/2004 | LeJeune et al. | |
| 6,808,908 B2 | 10/2004 | Yao et al. | |
| 6,905,733 B2 | 6/2005 | Russell et al. | |
| 6,936,445 B2 | 8/2005 | Kawabe et al. | |
| 7,381,552 B2 | 6/2008 | Menzler et al. | |
| 7,521,214 B2 | 4/2009 | Yaku et al. | |
| 2002/0015985 A1 | 2/2002 | Takahashi et al. | |
| 2004/0106178 A1 | 6/2004 | Ackerman et al. | |
| 2007/0087418 A1 | 4/2007 | Mazeaud et al. | |
| 2008/0199932 A1 | 8/2008 | Hanzel et al. | |
| 2009/0035831 A1 | 2/2009 | Othman et al. | |
| 2009/0061499 A1 | 3/2009 | Stloukal et al. | |

FOREIGN PATENT DOCUMENTS

| | | |
|---|---|---|
| CN | 1800341 A | 7/2006 |
| JP | 02 109986 A | 4/1990 |
| JP | 02 219575 A | 9/1990 |
| JP | 02 257882 A | 10/1990 |
| JP | 04 258291 A | 9/1992 |
| WO | WO 90/15868 | 12/1990 |
| WO | WO 02/085519 A2 | 10/2002 |
| WO | WO 2007/140595 A1 | 12/2007 |

OTHER PUBLICATIONS

Eldin et al., "Beta-Galactosidase Immobilization on Premodified Teflon Membranes Using gamma-Radiation Grafting", Journal of Applied Polymer Science, vol. 68, 625-636 (1998).*
Wang et al., "Immobilization of lipase with a special microstructure in composite hydrophilic CA/hydrophobic PTFE membrane for the chiral separation of racemic ibuprofen", Journal of Membrane Science, 293, (2007), 133-141.*
4.1.1.2 oxalate decarboxylase enzyme classification from Brenda < http://www.brenda-enzymes.org/php/result_flat.php4?ecno=4.1.1.2 > downloaded Nov. 20, 2012.*
Definition of hydrolytic enzyme < http://www.biology-online.org/dictionary/Hydrolytic_enzymes > downloaded Nov. 20, 2012.*
Hidaka et al., "Trimeric Crystal Structure of the Glycoside Hydrolase Family 42 b-Galactosidase from *Thermus thermophilus* A4 and the Structure of its Complex with Galactose", J. Mol. Biol. (2002) 322, 79-91.*
Hilal et al., "Immobilization of cross-linked lipase aggregates within microporous polymeric membranes", Journal of Membrane Science, 2004, 238: 131-141.*
Tsai & Shaw, "Selection of hydrophobic membranes in the lipase-catalyzed hydrolysis of olive oil", J. of Mem. Sci., 1998, 146:1-8.*
Gupta et al., "Tune to immobilize lipases on polymer membranes: Techniques, factors and prospects", Biocatalysis and Agricultural Biotechnology, 2013, 2:171-190.*
Deshmukh, S. P. and Li, K.; "Effect of Ethanol Composition in Water Coagulation Bath on Morphology of PVDF Hollow Fibre Membranes"; Journal of Membrane Science; 1998; 150, pp. 75-85.

(Continued)

*Primary Examiner* — Suzanne M Noakes
(74) *Attorney, Agent, or Firm* — Jennifer R. Knight

(57) ABSTRACT

Enzyme catalyst immobilized on porous fluoropolymer supports. Catalytically active enzymes can be bound to a variety of fluoropolymer supports for use as a reaction catalyst. Moreover, consistently high rate of conversion during catalyst re-use over time is achieved. Furthermore, inactive enzyme catalyst can be stripped from the support and fresh enzyme can be bound to the support to achieve the original conversion rate. The immobilization of catalytic enzymes on porous fluoropolymers is a viable and novel technology for the preparation of advantaged catalysts.

23 Claims, No Drawings

(56) References Cited

OTHER PUBLICATIONS

Hsuanyu, Yuchiong et al.; "A Functionalized Highly Porous Polymer for Enzyme Immobilization"; reprinted from American Laboratory News Jun./Jul. 2007; http://www.sunstorm-research.com/PDF%20files/Enzyme%202007%20%20Am%20Lab.pdf.

Huo, Y. et al; "Immobilization of Glucoamylase onto Novel Porous Polymer Supports of Vinylene Carbonate and 2-hydroxyethyl Methacrylate"; Appl. Biochem Biotechnol.; Nov. 2004; 119(2), pp. 121-132.

Kurumada, Ken-Ichi et al.; "Structure Generation in PTFE Porous Membranes Induced by the Uniaxial and Biaxial Stretching Operations"; Journal of Membrane Science; 1998; 149, pp. 51-57.

Roig, M. G. et al.; "Liver Alcohol Dehydrogenase Immobilized on Polyvinylidene Difluoride"; J. Chem. Tech. Biotechnology; 1990; 49, pp. 99-113.

Tanioka, Akihiko et al.; "Preparation and Properties of Enzyme-Immobilized Porous Polypropylene Films"; Journal of Colloid and Interface Science; Apr. 1, 1998; vol. 200, Issue 1, pp. 185-187.

Wöltinger, Jens et al.; "The Chemzyme Membrane Reactor in the Fine Chemicals Industry"; Organice Process Research & Development; 2001; 5 pp. 241-248.

Wöltinger, Jens et al.; "The Membrane Reactor in the Fine Chemicals Industry"; Applied Catalysis A: General; 2001; 221, pp. 171-185.

Xu, Jian et al.; "*Candida* Rugosa Lipase Immobilized by a Specially Designed Microstructure in the PVA/PTFE Composite Membrane"; Journal of Membrane Science; 2006, 281, pp. 410-416.

Xu, Jian et al.; "Immobilization of Lipase by Filtration into a Specially Designed Microstructure in the CA/PTFE Composite Membrane"; Journal of Molecular Catalysis; 2006; 42, pp. 55-63.

Notification of Transmittal of the International Search Report and the Written Opinion of the International Searching Authority, or the Declaration received in International Application No. PCT/US2011/045882 date of mailing Nov. 30, 2011.

Chu, Mingxing et al.; "A soft and flexible biosensor using a phospholipid polymer for continuous glucose monitoring"; Biomed Microdevices (2009) 11: 837-842.

Hilal, N. et al.; "Immobilization of cross-linked lipase aggregates within microporous polymeric membranes"; Journal of Membrane Science 238 (2004) 131-141.

Hu, Yu et al.; "Modeling of a biphasic membrane reactor catalyzed by lipase immobilized in a hydrophilic/hydrophobic composite membrane"; Journal of Membrane Science 308 (2008) 242-249.

Ying, Lei et al.; Covalent immobilization of glucose oxidase on microporous membranes prepared from poly(vinylidene fluoride) with grafted poly(acrylic acid) side chains; Journal of Membrane Science 208 (2002) 361-374.

Jian, Xu et al.; "Effect of Hydrophobic or Hydrophilic Performance of Membranes on Lipase Immobilization"; Journal of Chemical Engineering of Chinese Universities, vol. 20, No. 3; Jun. 30, 2006; pp. 395-397 (English abstract and original language).

\* cited by examiner

ENZYME CATALYST IMMOBILIZED ON POROUS FLUOROPOLYMER SUPPORT

BACKGROUND OF THE INVENTION

Enzyme catalysts are useful for chemical transformations in industrial processes. Benefits of enzyme catalysts include catalytic activity at relatively low temperatures, unique reactions and products, and the potential for high selectivity. Immobilization on a solid support stabilizes an enzyme and prolongs its catalytic lifetime. Immobilization also facilitates removal of the catalyst from the reaction for re-use.

Enzymes are typically supported on particles, with ion exchange resins and modified silica particles among the most common supports. Enzymes immobilized on ion exchange resins are very common. Weakly acidic and weakly basic ion exchange resins are used for immobilizing enzymes. Most ion-exchange resins are based on crosslinked polystyrene in the form of small beads. In a batch reaction, agitation can pulverize the ion exchange resin beads, which reduces enzyme activity, complicates catalyst removal from the process and prevents re-use of the immobilized catalyst. Silica particles used to immobilize enzymes are often very small, complicating removal from a batch reaction. In a packed bed column, the packing of the ion exchange particles or the small particle size of the typical silica particle can result in high back pressures and difficulty flowing a reaction mix through the catalyst bed, and can eventually lead to plugging. In any reaction configuration, ion exchange particles are subject to degradation or even additional crosslinking in the reaction conditions such as in presence of solvents, at high temperatures, or in extreme pH conditions.

Exclusion membranes are small-pore membranes which restrict the movement of a homogeneous enzyme or whole-cell catalyst in a reaction system. In exclusion membranes, the enzyme is active in solution on one side of the membrane rather than immobilized on both sides of the membrane. Indeed, the membrane is used only for selective separation, and the optimal pore size is restricted by the size of the enzyme catalyst and the product. The effective pore size must exclude the enzyme catalyst while allowing the product to pass through. Biphasic and asymmetric membrane reactors employ an enzyme catalyst deposited by filtration as an insoluble particle at the interface of a hydrophobic and hydrophilic membrane to facilitate a hydrolysis reaction on the hydrophilic side of the reactor system. The hydrophilic membrane must have a pore size smaller than the size of the enzyme catalyst so as to exclude transmission of the enzyme catalyst into the aqueous phase, thus serving as an exclusion membrane. Asymmetric porous fluoropolymer membranes have been surface-modified to yield a hydrophobic and a hydrophilic surface. An enzyme catalyst is immobilized to only one surface of the asymmetrical membrane.

One object of the present invention is to overcome the limitations presented by immobilizing enzyme catalysts onto a particulate support, namely the size and structural weaknesses and single use feature. Another object of the invention is to overcome the limitations presented by association of an enzyme catalyst with an exclusion or asymmetrical porous support, namely, the use of only one surface.

SUMMARY OF THE INVENTION

An embodiment of the present invention concerns an immobilized catalyst comprising a porous fluoropolymer support having at least one layer and at least one enzyme catalyst immobilized to the support, wherein the support is selected from the group consisting of a membrane, a film, a tape, a fiber, a hollow fiber, a tube, a braid, and a sponge, the effective pore size of each layer of the support is greater than the size of the enzyme catalyst, and the catalyst maintains catalytic activity for between 2 and 50 uses.

Another embodiment concerns an immobilized catalyst comprising a porous fluoropolymer membrane and at least one catalyst immobilized to the support, wherein the enzyme catalyst is immobilized on both surfaces of the membrane; the effective pore size of each layer of the membrane is greater than the size of the enzyme catalyst, and the catalyst maintains catalytic activity for between 2 and 50 uses.

Another embodiment concerns a cartridge comprising an immobilized catalyst comprising a porous fluoropolymer membrane and at least one catalyst immobilized to the support, wherein the enzyme catalyst is immobilized on both surfaces of the membrane; the effective pore size of each layer of the membrane is greater than the size of the enzyme catalyst, and the catalyst maintains catalytic activity for between 2 and 50 uses.

Another embodiment concerns a reactor comprising the immobilized catalyst.

Yet another embodiment concerns a method of producing an immobilized catalyst comprising contacting at least one enzyme catalyst and the support, wherein the support has at least one layer and is selected from the group consisting of a membrane, a film, a tape, a fiber, a hollow fiber, a tube, a braid, and a sponge; and the effective pore size of each layer of the support is greater than the size of the catalyst, and the catalyst maintains catalytic activity for between 2 and 50 uses.

Still another embodiment concerns a method of producing a fuel or chemical comprising contacting at least one reactant with at least one immobilized enzyme catalyst to produce the chemical, wherein the enzyme catalyst is immobilized on a porous fluoropolymer support; the support has at least one layer and is selected from the group consisting of membrane, a film, a tape, a fiber, a hollow fiber, a tube, a braid, and a sponge; the effective pore size of each layer of the support is greater than the size of the enzyme catalyst, and the catalyst maintains catalytic activity for between 2 and 50 uses.

DETAILED DESCRIPTION OF THE INVENTION

According to an embodiment, the present invention pertains to an immobilized catalyst comprised of an enzyme catalyst immobilized on a porous fluoropolymer support such as, for example, a symmetrical porous fluoropolymer support. The present invention also pertains to methods of making and using an immobilized catalyst.

According to an embodiment, an enzyme catalyst may be immobilized via non-covalently binding the catalyst to a porous fluoropolymer support. Moreover, unlike an exclusion membrane system, the effective pore size of the fluoropolymer support may exceed the size of the enzyme catalyst. The support may contain one or more symmetrical layers, with each porous layer having an effective pore size exceeding the size of the enzyme catalyst. A benefit of a support with a pore size exceeding the size of the enzyme catalyst is that the enzyme catalyst may be adsorbed or non-covalently bound and thus immobilized to more than one surface of the porous fluoropolymer support (e.g. front and back planar surface of a film). Support materials made from fluoropolymers are chemically inert and able to withstand harsh reaction conditions such as high temperatures or pH extremes, and are thus acceptable for use in industrial processes.

According to an embodiment, one or more enzyme catalysts can be immobilized on a porous fluoropolymer support.

The preparation, morphology and performance of fluoropolymer filtration and pervaporation membranes have been studied. A fluoropolymer is a fluorocarbon based polymer with multiple strong carbon-fluorine bonds. It is characterized by a high resistance to solvents, acids, and bases. Examples of fluoropolymers include PTFE polytetrafluoroethylene (Teflon); PVDF polyvinylidene difluoride (Kynar); ETFE polyethylenetetrafluoroethylene; PCTFE polychlorotrifluoroethylene; PVF polyvinylfluoride; PFA perfluoroalkoxy polymer resin; FEP fluorinated ethylene-propylene; ECTFE polyethylenechlorotrifluoroethylene (Halar), and PFPE Perfluoropolyether. PVDF and PTFE are commonly used fluoropolymers for porous materials. A copolymer or other structural or functional material may be associated with the fluoropolymer, but is not required.

Porous fluoropolymer supports can be prepared according to published protocols. (e.g. Handbook of Filter Media, Derek Purchas and Ken Sutherland, 2002). Examples of the preparation of porous fluoropolymer supports include solvent casting, a process in which the fluoropolymer is dissolved in a suitable solvent system, then cast into the desired form, such as a film, and exposed to a non-solvent to gel. Evaporation of the solvent from the gelled polymer matrix creates pores. Pore size depends on the concentration of the polymer in the solvent, additives, the nature of the non-solvent, and other factors such as temperature. Porous fibers may be made similarly by a wet-spinning fiber process, resulting in hollow or non-hollow fibers. Another process for creating a porous fluoropolymer support includes mechanical stretching. For example, porous expanded PTFE membranes can be made by biaxial stretching of a PTFE film to physically separate the fibrils in two dimensions, after which the pore size can be fixed with a heat treatment.

The porous fluoropolymer support material may be in the form of a membrane, film, tape, fiber, hollow fiber, tube, braid, sponge, foam or particle. Various porous fluoropolymer materials are available commercially. The following list is meant to illustrate examples, not to be exhaustive:

| Supplier | |
| --- | --- |
| Alfa Laval | DSS FSMO, 45PP Fluoropolymer |
| Koch Membrane Systems | HFM-707; Supported PVDF |
| Koch | HFM-116; Supported PVDF copolymer |
| Koch | HFM-180; Supported PVDF |
| Koch | HFM-100; Supported PVDF |
| Koch | HFM-183; Supported PVDF |
| Pall | PTF045LR0P PTFE on non-woven polypropylene |
| Pall | PTF045LH0P PTFE on non-woven polyester |
| Pall | PTF045LD0A PTFE on non-woven polypropylene |
| Pall | BioTrace PVDF |
| Millipore | Immobilon-P PVDF |
| Microdyn Nadir | PM UV150 PVDF |
| Microdyn Nadir | PM UV200 PVDF |
| Microdyn Nadir | PM MV020 PVDF |
| Inertex | Expanded Teflon sponge, 0.5 mm thick |
| JSC Plastpolymer | Poroflex porous fluoropolymer braid |
| Interplastic, Inc | PTFE sponge |
| Inertech, Inc | Inertex SQ-S expanded PTFE |
| Acton Technologies/Arkema Inc. | Kynar Ultraflex ™ PVDF Foam |

According to an embodiment, the fluoropolymer support material is porous. Moreover, the effective pore size of the support material can exceed the size of the enzyme catalyst and thus, the support material is not intended to be an exclusion membrane. Pore size can range from less than 15,000 MWCO to greater than 1.0 micron. For example, the pore size can range from about 50,000 MWCO to 0.5 microns, or from 100,000 MWCO to about 0.45 microns. Both microfiltration and ultrafiltration media are suitable support materials. Flow through the pores of the support material is not required, such as in the case of a sponge or foam, which has a porous surface but may not permit material to flow through. For porous materials in this range, pore size can be indicated either by a molecular weight cut-off (MWCO) or by a pore diameter, usually expressed in microns ($10^{-6}$ meters). Enzyme catalysts vary in size, but can be measured either by molecular weight or by dimension, usually expressed in Angstroms ($10^{-10}$ meters). The sizes of many different enzymes can be found at various databases, such as the RCSB Protein Data Bank. Enzyme catalysts can range in size from less than 12,000 MW (12 kilodaltons, kDa) as in the case of ribonucleases, up to greater than 300,000 MW in the case of multimeric enzymes. Most commercially important enzyme catalysts range in size from 30,000 MW to about 100,000 MW. For example, fungal lipases, a class of commercial enzymes, average about 40,000 MW with an average diameter of less than 100 Angstroms (0.01 microns). The pores in a material with a MWCO of 50,000 or a pore size of 0.02 microns or greater would exceed the average size of a fungal lipase.

According to an embodiment, the porous fluoropolymer support is symmetrical. Moreover, while the support may include more than one layer, such as a structural backing material on a porous fluoropolymer membrane, the effective pore size of each layer is greater than the size of the enzyme catalyst. For example, the average diameter of the pores is larger than the average diameter of the enzyme catalyst. When the pore size is greater than the size of the enzyme catalyst, the enzyme catalyst can contact all surfaces of the symmetrical support.

In one embodiment, the fluoropolymer support is pre-wet with water, an alcohol or polyol. Unless they have been surface-treated, fluoropolymers are usually hydrophobic materials. In order to contact an aqueous solution of enzyme with the hydrophobic surface of the porous support material, it should be pre-wet, usually with an alcohol such as ethanol or methanol. During the manufacturing process, the fluoropolymer may be dissolved in a solvent, a film cast from the solution, then the film contacted with a non-solvent to precipitate the film and create pores. The non-solvent may contain water or an alcohol or polyol, or be easily exchanged with water, alcohol or polyol, leaving the porous support material in a pre-wet condition. Sometimes the porous fluoropolymer support material is supplied wet or pre-wet with water, an alcohol or a polyol such as glycerol. If the porous material is supplied dry, then the surface may be wetted with an alcohol prior to contacting it with the enzyme. Ethanol, methanol, propanol, Isopropanol, butanol, Isobutanol, tert-butanol and other lower alcohols are all acceptable pre-wetting agents. The pre-wetting agent is typically removed by rinsing prior to contacting the support with the enzyme catalyst.

The enzyme catalyst can be any polypeptide with catalytic activity. For example, the enzyme catalyst may be in the form of an isolated enzyme, a mixture of enzymes, a cell extract, or a whole cell. The enzyme catalyst can include a hydrolytic enzyme, transferase, isomerase, lyase, ligase, dehydratase, catalase, hydroxylase, nitrilase, nuclease, polymerase, kinase, or phosphatase. In one embodiment, the enzyme catalyst is a hydrolytic enzyme such as a lipase, esterase or protease or amidase.

In one embodiment, the enzyme catalyst is in solution. For example, the enzyme can be in a predominantly aqueous solution. If the enzyme is in lyophilized form, it can be reconstituted with water. The enzyme solution may optionally contain a surfactant, salts, a buffering agent, polymers, cofactors or preservatives intended to solublize, stabilize or promote the activity of the enzyme catalyst. The enzyme catalyst may also be a cell extract in a predominantly aqueous solution, or a whole cell.

According to an embodiment, the enzyme solution can be contacted with the fluoropolymer support. Moreover, contact can be effected by any means including cross flow, immersion, agitation, rotation or stirring. According to an embodiment, contact is maintained for several minutes to several days, for example from about 0.5 hours to about 144 hours, from about 2 hours to about 48 hours; at a temperature of from about 0 to about 100 degrees C.; from about 4 to about 80 degrees C.; or from about 15 to about 50 degrees C.

The enzyme is catalytically active after immobilization. Moreover, the immobilized enzyme catalyst can be used as a catalyst for many different reactions. For example, the reaction catalyzed can be an esterification, transesterification or interesterification, peptide bond formation, hydrolysis, transferase, isomerization, ligation, dehydration, hydroxylation, nitrilation, or polymerization. Moreover, the immobilized catalyst maintains enzyme binding and activity even after multiple re-uses. For example, the immobilized catalyst maintains catalytic activity for between 2 and 50 reuses, between 3 and 30 reuses or even between 5 and 10 reuses. Maintaining catalytic activity is intended to mean that the immobilized catalyst maintains at least 70% of initial catalytic activity after at least 10 uses, at least 80% of initial catalytic activity after at least 10 reuses, or even at least 90% of initial catalytic activity after at least 10 reuses.

According to an embodiment the immobilized catalyst is non-covalently bound to the support and can be removed from the support, such as with a surfactant and/or protease. The cleaned support can be re-used to immobilize fresh catalytically active enzyme. Conditions for re-immobilizing enzyme catalyst are essentially as described above.

Applications of an enzyme catalyst immobilized on a porous fluoropolymer support include the use of the immobilized enzyme catalyst as a process catalyst for the manufacture of fuels and chemicals. The catalyst may function to produce an intermediate or a final product or both. Multiple enzymes catalysts for multiple transformations may be bound to the same or sequential supports.

A flat sheet membrane, sponge, braid, fiber, hollow fiber or particle can be loaded with catalyst, then assembled into a reactor system. A pre-assembled reactor system, such as a flow-through or zero to 100% by-pass cartridge, containing the porous fluoropolymer support, can be loaded in situ with enzyme catalyst, such as by immersion in the enzyme solution or flow of the enzyme solution through or across the support.

The products that can be made using an enzyme catalyst immobilized on a porous fluoropolymer support include fuels and chemicals. The products may be final products or intermediates in a process. The products that can be made include esters, amides, amines, alcohols, diols, polyols, aldehydes, acids, polymers, thiols, or mixtures thereof. These products can be achiral, racemic, or enantiomerically enriched.

Benefits of an enzyme-catalyzed reaction include the potential for highly selective reactions at moderate temperatures. High reaction selectivity can reduce the formation of unwanted by-products and reduce or eliminate downstream processing and its associated inputs (e.g. filtering agents, solvents, energy, and equipment). Reactions performed at moderate temperatures are less energy-intensive, and also tend to result in fewer unwanted by-products. Additional benefits of the use of a porous fluoropolymer support include the possibility of performing selective separations of products or by-products.

EXAMPLES

As can be seen in the following examples, high catalyst activity was achieved with membrane immobilization methods and the enzymatic activity was maintained for multiple re-uses. In addition, enzyme catalyst could be removed from the membrane surface with detergent treatment, and the membrane could be re-loaded with fresh catalyst with no loss in catalytic activity. Porous fluoropolymer membranes (PVDF and PTFE) had the highest enzyme binding and subsequent catalytic activity of the membranes tested. Both supported and unsupported porous fluoropolymer membranes were among the better performers.

An initial screening of a wide variety of different membrane materials indicated that fluoropolymer membranes were preferable for binding an active biocatalyst. Furthermore, fluoropolymer supports resulted in both enzyme binding and activity with a long lifetime (at least 10 re-uses without reduction in catalytic activity). In these initials screening experiments, Immobilon-P, an unsupported microporous PVDF membrane from Millipore, performed well, and was selected for use as a standard support in all subsequent experiments. Additional membranes were selected as detailed in Table 1.

TABLE 1

Membranes used as supports for enzyme immobilization in Examples 1-9.

| Label | Supplier | Material | Pore size/ MWCO | Supplied |
|---|---|---|---|---|
| FSMO | Alfa Laval | DSS FSMO, 45PP Fluoropolymer | 0.45 micron | dry |
| K100 | Koch | HFM-100; Supported PVDF | 50,000 MWCO | wet |
| K116 | Koch | HFM-116; Supported PVDF copolymer | 50,000 MWCO | wet |
| K180 | Koch | HFM-180; Supported PVDF | 100,000 MWCO | wet |
| K183 | Koch | HFM-183; Supported PVDF | 100,000 MWCO | wet |
| K707 | Koch | HFM-707; Supported PVDF | 120,000 MWCO | wet |
| PTF-LR | Pall | PTF045LR0P PTFE on non-woven polypropylene | 0.45 micron | dry |
| PTF-LH | Pall | PTF045LH0P PTFE on non-woven polyester | 0.45 micron | dry |
| PTF-LD | Pall | PTF045LD0A PTFE on non-woven polypropylene | 0.45 micron | dry |
| PVDF-P | Pall | BioTrace PVDF | 0.45 micron | dry |
| UV150 | Microdyn Nadir | PM UV150 PVDF | 150,000 MWCO | dry |
| UV200 | Microdyn Nadir | PM UV200 PVDF | 200,000 MWCO | dry |
| MV020 | Microdyn Nadir | PM MV020 PVDF | 0.2 micron | dry |
| PVDF-M | Millipore | Immobilon-P PVDF | 0.45 micron | dry |
| ISQ-S | Inertex | Expanded Teflon sponge, 0.5 mm thick | Not applicable | dry |

Standard Immobilization Protocol:

Enzyme loading: A 3 cm×9 cm membrane strip was wound and positioned inside the base of an 8 dram glass vial. The strip overlapped slightly around the inner diameter of the vial. With supported membranes, the fluoropolymer side was positioned facing in. The dry membranes were pre-wet with 1 ml ethanol and drained well. Each membrane was washed with 10 ml water and equilibrated at least 10 minutes, then drained well. The water removed the ethanol from the ethanol-wet membranes, or else helped to remove the preservative solution (usually containing glycerol) from the membranes that were supplied wet. The pre-wet and rinsed membranes were then equilibrated with 10 ml of binding solution for 10 minutes, then drained. To each vial another 5 ml of binding solution was added, then 1 ml of the enzyme stock solution was added. The vials were capped and secured in secondary containers, then rotated horizontally at 4 deg C. for 24 h to continually distribute the enzyme solution on the surface of the membrane. After 24 h, the protein solution was sampled to determine protein binding by difference (before and after immobilization) using a Bradford assay and an albumin standard curve. The excess enzyme solution was drained, the membranes were rinsed once with the appropriate wash buffer (10 ml), then drained and equilibrated in the same wash buffer (10 ml) for at least 15 minutes. The washed membranes were drained of excess fluid and stored at 4 deg C. (damp) until the activity assay was performed.

Activity assay for lipases (Examples 1-9; Ethylhexyl palmitate synthesis): Any excess liquid was removed from the bottom of the vial with a pipette or cotton swab, and if needed, a #11 or #12 o-ring was added to the bottom of the vials containing supported membranes to prevent membrane curling at the reaction temperature. A stir bar was added to each vial, then the reactants were weighed separately into each vial: 5 g palmitic acid+2.5 g 2-ethylhexanol. The reactants were melted together at 65 deg C. for 30 minutes, then the vials were transferred to a stirred heat block and stirred at 60 deg C. (800 rpm stir speed). The percent conversion to product (Ethylhexyl palmitate) was estimated at 4 and 24 hours by sampling 40 ul of the reaction mix into a vial and adding 2 ml methanol. The reaction mix was analyzed by gas chromatography. The three reactant and product peaks were integrated and the area % of the product peak was recorded. This analytical method is a good approximation of weight conversion based on NMR data obtained for several of the same samples. After 24 hours, the reaction mix was removed with a pipette and the used membranes were stored at room temperature.

Example 1

Immobilization of Catalytically Active Lipase to Fluoropolymer Supports Under Different pH Conditions Both the pH at which the enzyme was bound to the support and the pH at which the protein-loaded membrane was washed were varied. The pH of an enzyme solution can have a profound impact on the surface charge of a protein, influencing both how it interacts with a support material and how it interacts with substrates for catalysis. We found that pH did impact protein binding, activity and stability, and that the ideal pH conditions varied among the different support materials.

Enzyme Catalyst: The enzyme catalyst was a *Candida antarctica* lipase B solution manufactured and sold by Novozymes as Lipozyme CALB L. The solution contains approximately 2 mg protein/ml, as determined by a Bradford protein assay.

Support Materials: Membranes are detailed in Table 1.

pH Conditions: Four pH levels were selected (2, 4, 7, 10) for both binding protein to the membrane and for the washing step, yielding a set of 16 different pH conditions for each support material. Hydrion buffer powders were used to make the buffers, and were reconstituted according to the supplied directions, except that the buffer preservative was omitted. Hydrion buffer powders are made by MicroEssential and sold by Fluka (cat #239151 for the set of pH 2-11).

The results of the enzyme activity assay are reported in Table 2. Each membrane support was used to immobilize the lipase catalyst using all 16 possible combinations of binding and wash buffer. Then each supported catalyst system was used in an esterification reaction to synthesize Ethylhexyl palmitate. In all cases, the maximum conversion rate for each membrane support system was greater than a no-catalyst control (2% conversion after 4 h and 10% conversion after 24 h at 60 degrees C.).

Immobilization of the enzyme to the support was effective between pH 2 and pH 10. The immobilization conditions resulting in the maximum conversion for each membrane support are bolded.

| | pH bind | pH wash | % conversion 4 h | % conversion 24 h |
|---|---|---|---|---|
| FSMO | 2 | 2 | 2 | 9 |
| FSMO | 2 | 4 | 3 | 23 |
| FSMO | 2 | 7 | 3 | 35 |
| FSMO | 2 | 10 | 3 | 23 |
| FSMO | 4 | 2 | 2 | 10 |
| FSMO | 4 | 4 | 3 | 42 |
| FSMO | 4 | 7 | 4 | 33 |
| FSMO | 4 | 10 | 3 | 24 |
| FSMO | 7 | 2 | 2 | 9 |
| FSMO | 7 | 4 | 4 | 37 |
| FSMO | 7 | 7 | 4 | 26 |
| FSMO | 7 | 10 | 3 | 23 |
| FSMO | 10 | 2 | 2 | 9 |
| FSMO | 10 | 4 | 2 | 22 |
| FSMO | 10 | 7 | 3 | 20 |
| FSMO | 10 | 10 | 2 | 18 |
| K100 | 2 | 2 | 6 | 26 |
| K100 | 2 | 4 | 17 | 65 |
| K100 | 2 | 7 | 22 | 71 |
| K100 | 2 | 10 | 15 | 55 |
| K100 | 4 | 2 | 8 | 36 |
| K100 | 4 | 4 | 27 | 73 |
| K100 | 4 | 7 | 30 | 71 |
| K100 | 4 | 10 | 21 | 64 |
| K100 | 7 | 2 | 7 | 38 |
| K100 | 7 | 4 | 19 | 68 |
| K100 | 7 | 7 | 20 | 66 |
| K100 | 7 | 10 | 24 | 63 |
| K100 | 10 | 2 | 8 | 36 |
| K100 | 10 | 4 | 20 | 68 |
| K100 | 10 | 7 | 21 | 67 |
| K100 | 10 | 10 | 22 | 63 |
| K116 | 2 | 2 | 4 | 26 |
| K116 | 2 | 4 | 12 | 46 |
| K116 | 2 | 7 | 10 | 43 |
| K116 | 2 | 10 | 8 | 35 |
| K116 | 4 | 2 | 4 | 16 |
| K116 | 4 | 4 | 11 | 50 |
| K116 | 4 | 7 | 10 | 38 |
| K116 | 4 | 10 | 8 | 38 |
| K116 | 7 | 2 | 5 | 22 |
| K116 | 7 | 4 | 10 | 47 |
| K116 | 7 | 7 | 9 | 38 |
| K116 | 7 | 10 | 8 | 39 |

| | pH bind | pH wash | % conversion 4 h | % conversion 24 h |
|---|---|---|---|---|
| K116 | 10 | 2 | 5 | 20 |
| K116 | 10 | 4 | 9 | 39 |
| K116 | 10 | 7 | 9 | 42 |
| K116 | 10 | 10 | 7 | 33 |
| K180 | 2 | 2 | 3 | 17 |
| K180 | 2 | 4 | 6 | 48 |
| K180 | 2 | 7 | 6 | 58 |
| K180 | 2 | 10 | 9 | 58 |
| K180 | 4 | 2 | 5 | 26 |
| K180 | 4 | 4 | 9 | 62 |
| K180 | 4 | 7 | 12 | 64 |
| K180 | 4 | 10 | 11 | 54 |
| K180 | 7 | 2 | 4 | 30 |
| K180 | 7 | 4 | 6 | 54 |
| K180 | 7 | 7 | 15 | 65 |
| K180 | 7 | 10 | 14 | 63 |
| K180 | 10 | 2 | 5 | 35 |
| K180 | 10 | 4 | 7 | 61 |
| K180 | 10 | 7 | 8 | 60 |
| K180 | 10 | 10 | 11 | 60 |
| K183 | 2 | 2 | 2 | 12 |
| K183 | 2 | 4 | 13 | 70 |
| K183 | 2 | 7 | 37 | 75 |
| K183 | 2 | 10 | 28 | 67 |
| K183 | 4 | 2 | 2 | 11 |
| K183 | 4 | 4 | 7 | 36 |
| K183 | 4 | 7 | 40 | 78 |
| K183 | 4 | 10 | 30 | 71 |
| K183 | 7 | 2 | 2 | 11 |
| K183 | 7 | 4 | 7 | 59 |
| K183 | 7 | 7 | 31 | 73 |
| K183 | 7 | 10 | 26 | 67 |
| K183 | 10 | 2 | 3 | 19 |
| K183 | 10 | 4 | 7 | 63 |
| K183 | 10 | 7 | 38 | 77 |
| K183 | 10 | 10 | 27 | 68 |
| K707 | 2 | 2 | 2 | 10 |
| K707 | 2 | 4 | 2 | 15 |
| K707 | 2 | 7 | 3 | 25 |
| K707 | 2 | 10 | 2 | 10 |
| K707 | 4 | 2 | 2 | 8 |
| K707 | 4 | 4 | 3 | 15 |
| K707 | 4 | 7 | 2 | 14 |
| K707 | 4 | 10 | 4 | 21 |
| K707 | 7 | 2 | 2 | 9 |
| K707 | 7 | 4 | 2 | 11 |
| K707 | 7 | 7 | 6 | 40 |
| K707 | 7 | 10 | 3 | 36 |
| K707 | 10 | 2 | 2 | 8 |
| K707 | 10 | 4 | 2 | 11 |
| K707 | 10 | 7 | 2 | 11 |
| K707 | 10 | 10 | 3 | 18 |
| PTF-LR | 2 | 2 | 6 | 19 |
| PTF-LR | 2 | 4 | 16 | 55 |
| PTF-LR | 2 | 7 | 12 | 48 |
| PTF-LR | 2 | 10 | 3 | 13 |
| PTF-LR | 4 | 2 | 4 | 13 |
| PTF-LR | 4 | 4 | 16 | 57 |
| PTF-LR | 4 | 7 | 14 | 51 |
| PTF-LR | 4 | 10 | 3 | 19 |
| PTF-LR | 7 | 2 | 10 | 28 |
| PTF-LR | 7 | 4 | 13 | 53 |
| PTF-LR | 7 | 7 | 15 | 52 |
| PTF-LR | 7 | 10 | 4 | 20 |
| PTF-LR | 10 | 2 | 3 | 11 |
| PTF-LR | 10 | 4 | 9 | 40 |
| PTF-LR | 10 | 7 | 6 | 29 |
| PTF-LR | 10 | 10 | 2 | 11 |
| PTF-LH | 2 | 2 | 7 | 20 |
| PTF-LH | 2 | 4 | 18 | 56 |
| PTF-LH | 2 | 7 | 15 | 51 |
| PTF-LH | 2 | 10 | 3 | 17 |
| PTF-LH | 4 | 2 | 10 | 35 |
| PTF-LH | 4 | 4 | 18 | 57 |
| PTF-LH | 4 | 7 | 16 | 52 |
| PTF-LH | 4 | 10 | 5 | 26 |
| PTF-LH | 7 | 2 | 14 | 49 |
| PTF-LH | 7 | 4 | 19 | 60 |
| PTF-LH | 7 | 7 | 17 | 55 |
| PTF-LH | 7 | 10 | 4 | 21 |
| PTF-LH | 10 | 2 | 3 | 16 |
| PTF-LH | 10 | 4 | 8 | 35 |
| PTF-LH | 10 | 7 | 6 | 28 |
| PTF-LH | 10 | 10 | 2 | 13 |
| PTF-LD | 2 | 2 | 13 | 29 |
| PTF-LD | 2 | 4 | 24 | 66 |
| PTF-LD | 2 | 7 | 31 | 71 |
| PTF-LD | 2 | 10 | 5 | 27 |
| PTF-LD | 4 | 2 | 19 | 48 |
| PTF-LD | 4 | 4 | 21 | 67 |
| PTF-LD | 4 | 7 | 24 | 69 |
| PTF-LD | 4 | 10 | 8 | 36 |
| PTF-LD | 7 | 2 | 15 | 47 |
| PTF-LD | 7 | 4 | 22 | 69 |
| PTF-LD | 7 | 7 | 25 | 68 |
| PTF-LD | 7 | 10 | 10 | 43 |
| PTF-LD | 10 | 2 | 4 | 13 |
| PTF-LD | 10 | 4 | 12 | 46 |
| PTF-LD | 10 | 7 | 12 | 45 |
| PTF-LD | 10 | 10 | 3 | 17 |
| PVDF-P | 2 | 2 | 17 | 53 |
| PVDF-P | 2 | 4 | 29 | 74 |
| PVDF-P | 2 | 7 | 23 | 69 |
| PVDF-P | 2 | 10 | 19 | 59 |
| PVDF-P | 4 | 2 | 18 | 53 |
| PVDF-P | 4 | 4 | 25 | 68 |
| PVDF-P | 4 | 7 | 22 | 67 |
| PVDF-P | 4 | 10 | 14 | 53 |
| PVDF-P | 7 | 2 | 16 | 56 |
| PVDF-P | 7 | 4 | 23 | 66 |
| PVDF-P | 7 | 7 | 18 | 64 |
| PVDF-P | 7 | 10 | 19 | 56 |
| PVDF-P | 10 | 2 | 18 | 54 |
| PVDF-P | 10 | 4 | 26 | 68 |
| PVDF-P | 10 | 7 | 25 | 68 |
| PVDF-P | 10 | 10 | 17 | 56 |
| UV150 | 2 | 2 | 4 | 18 |
| UV150 | 2 | 4 | 21 | 69 |
| UV150 | 2 | 7 | 29 | 76 |
| UV150 | 2 | 10 | 17 | 65 |
| UV150 | 4 | 2 | 4 | 23 |
| UV150 | 4 | 4 | 15 | 61 |
| UV150 | 4 | 7 | 23 | 73 |
| UV150 | 4 | 10 | 21 | 69 |
| UV150 | 7 | 2 | 4 | 18 |
| UV150 | 7 | 4 | 13 | 60 |
| UV150 | 7 | 7 | 26 | 70 |
| UV150 | 7 | 10 | 19 | 65 |
| UV150 | 10 | 2 | 3 | 25 |
| UV150 | 10 | 4 | 8 | 46 |
| UV150 | 10 | 7 | 15 | 66 |
| UV150 | 10 | 10 | 18 | 64 |
| PVDF-M | 2 | 2 | 12 | 47 |
| PVDF-M | 2 | 4 | 28 | 70 |
| PVDF-M | 2 | 7 | 23 | 70 |
| PVDF-M | 2 | 10 | 18 | 60 |
| PVDF-M | 4 | 2 | 14 | 46 |
| PVDF-M | 4 | 4 | 27 | 72 |
| PVDF-M | 4 | 7 | 28 | 74 |
| PVDF-M | 4 | 10 | 19 | 59 |
| PVDF-M | 7 | 2 | 16 | 54 |
| PVDF-M | 7 | 4 | 27 | 73 |
| PVDF-M | 7 | 7 | 27 | 73 |
| PVDF-M | 7 | 10 | 19 | 60 |
| PVDF-M | 10 | 2 | 13 | 47 |
| PVDF-M | 10 | 4 | 26 | 68 |
| PVDF-M | 10 | 7 | 24 | 70 |
| PVDF-M | 10 | 10 | 17 | 59 |
| ISQ-S | 2 | 2 | 21 | 54 |
| ISQ-S | 2 | 4 | 35 | 79 |

-continued

| support | pH bind | pH wash | % conversion 4 h | 24 h |
|---|---|---|---|---|
| ISQ-S | 2 | 7 | 37 | 81 |
| ISQ-S | 2 | 10 | 5 | 25 |
| ISQ-S | 4 | 2 | 19 | 59 |
| ISQ-S | 4 | 4 | 25 | 78 |
| ISQ-S | 4 | 7 | 29 | 82 |
| ISQ-S | 4 | 10 | 17 | 64 |
| ISQ-S | 7 | 2 | 15 | 48 |
| ISQ-S | 7 | 4 | 25 | 76 |
| ISQ-S | 7 | 7 | 32 | 79 |
| ISQ-S | 7 | 10 | 21 | 64 |
| ISQ-S | 10 | 2 | 20 | 60 |
| ISQ-S | 10 | 4 | 26 | 68 |
| ISQ-S | 10 | 7 | 24 | 64 |
| ISQ-S | 10 | 10 | 14 | 52 |

Example 2

Membrane Re-Use Experiments

During the pre-screening stage, it was noted that the performance of the fluoropolymer-immobilized enzyme catalyst improved after one or more uses, suggesting that there may be an equilibration period for the enzyme catalyst on these supports. Also, it was noticed that performing the Ethylhexyl palmitate test reaction at 70 degrees C. improved the reaction rate over the standard 60 degrees C. Several membranes from Example 1 were selected for additional activity assays to test these observations. The reaction conditions and analysis were repeated exactly as before. In a standard re-use experiment, the entire set of membrane reactors, representing all 16 immobilization conditions, was re-used, first at 60 degrees C. then again at 70 degrees C. The % conversion to product over time is summarized in Table 3.

TABLE 3

| support | pH bind | pH wash | use #1, 60 C. 4 h | 24 h | use #2, 60 C. 4 h | 24 h | use #3, 70 C. 4 h | 24 h |
|---|---|---|---|---|---|---|---|---|
| UV150 | 2 | 2 | 4 | 18 | 7 | 24 | 11 | 36 |
| UV150 | 2 | 4 | 21 | 69 | 40 | 77 | 53 | 86 |
| UV150 | 2 | 7 | 29 | 76 | 43 | 80 | 52 | 85 |
| UV150 | 2 | 10 | 17 | 65 | 29 | 68 | 42 | 79 |
| UV150 | 4 | 2 | 4 | 23 | 9 | 33 | 18 | 53 |
| UV150 | 4 | 4 | 15 | 61 | 38 | 78 | 56 | 90 |
| UV150 | 4 | 7 | 23 | 73 | 37 | 76 | 54 | 88 |
| UV150 | 4 | 10 | 21 | 69 | 32 | 72 | 41 | 78 |
| UV150 | 7 | 2 | 4 | 18 | 6 | 23 | 13 | 41 |
| UV150 | 7 | 4 | 13 | 60 | 33 | 74 | 57 | 89 |
| UV150 | 7 | 7 | 26 | 70 | 38 | 77 | 47 | 83 |
| UV150 | 7 | 10 | 19 | 65 | 30 | 71 | 42 | 80 |
| UV150 | 10 | 2 | 3 | 25 | 12 | 38 | 21 | 54 |
| UV150 | 10 | 4 | 8 | 46 | 33 | 75 | 55 | 85 |
| UV150 | 10 | 7 | 15 | 66 | 31 | 71 | 46 | 82 |
| UV150 | 10 | 10 | 18 | 64 | 26 | 67 | 45 | 78 |
| PTFLD | 2 | 2 | 13 | 29 | 12 | 37 | 18 | 49 |
| PTFLD | 2 | 4 | 24 | 66 | 40 | 76 | 51 | 82 |
| PTFLD | 2 | 7 | 31 | 71 | 29 | 72 | 34 | 72 |
| PTFLD | 2 | 10 | 5 | 27 | 16 | 47 | 26 | 61 |
| PTFLD | 4 | 2 | 19 | 48 | 20 | 59 | 32 | 68 |
| PTFLD | 4 | 4 | 21 | 67 | 40 | 79 | 56 | 86 |
| PTFLD | 4 | 7 | 24 | 69 | 31 | 72 | 41 | 76 |
| PTFLD | 4 | 10 | 8 | 36 | 19 | 53 | 33 | 70 |
| PTFLD | 7 | 2 | 15 | 47 | 22 | 56 | 34 | 70 |
| PTFLD | 7 | 4 | 22 | 69 | 39 | 76 | 57 | 88 |
| PTFLD | 7 | 7 | 25 | 68 | 30 | 71 | 42 | 79 |
| PTFLD | 7 | 10 | 10 | 43 | 22 | 59 | 38 | 70 |
| PTFLD | 10 | 2 | 4 | 13 | 4 | 14 | 7 | 24 |

TABLE 3-continued

| support | pH bind | pH wash | use #1, 60 C. 4 h | 24 h | use #2, 60 C. 4 h | 24 h | use #3, 70 C. 4 h | 24 h |
|---|---|---|---|---|---|---|---|---|
| PTFLD | 10 | 4 | 12 | 46 | 23 | 63 | 36 | 71 |
| PTFLD | 10 | 7 | 12 | 45 | 15 | 38 | 17 | 41 |
| PTFLD | 10 | 10 | 3 | 17 | 10 | 30 | 14 | 45 |
| K183 | 2 | 2 | 2 | 12 | 8 | 35 | 14 | 41 |
| K183 | 2 | 4 | 13 | 70 | 42 | 80 | 48 | 89 |
| K183 | 2 | 7 | 37 | 75 | 41 | 77 | 47 | 80 |
| K183 | 2 | 10 | 28 | 67 | 30 | 68 | 36 | 70 |
| K183 | 4 | 2 | 2 | 11 | 5 | 22 | 8 | 29 |
| K183 | 4 | 4 | 7 | 36 | 39 | 77 | 51 | 84 |
| K183 | 4 | 7 | 40 | 78 | 48 | 83 | 52 | 85 |
| K183 | 4 | 10 | 30 | 71 | 35 | 71 | 41 | 76 |
| K183 | 7 | 2 | 2 | 11 | 6 | 25 | 10 | 39 |
| K183 | 7 | 4 | 7 | 59 | 40 | 76 | 52 | 88 |
| K183 | 7 | 7 | 31 | 73 | 39 | 74 | 45 | 79 |
| K183 | 7 | 10 | 26 | 67 | 35 | 68 | 40 | 72 |
| K183 | 10 | 2 | 3 | 19 | 10 | 38 | 19 | 56 |
| K183 | 10 | 4 | 7 | 63 | 44 | 79 | 51 | 83 |
| K183 | 10 | 7 | 38 | 77 | 36 | 70 | 42 | 70 |
| K183 | 10 | 10 | 27 | 68 | 33 | 68 | 41 | 72 |
| ISQ-S | 2 | 2 | 21 | 54 | 26 | 59 | 31 | 65 |
| ISQ-S | 2 | 4 | 35 | 79 | 47 | 83 | 57 | 90 |
| ISQ-S | 2 | 7 | 37 | 81 | 46 | 83 | 57 | 87 |
| ISQ-S | 2 | 10 | 5 | 25 | 11 | 27 | 12 | 37 |
| ISQ-S | 4 | 2 | 19 | 59 | 29 | 63 | 36 | 70 |
| ISQ-S | 4 | 4 | 25 | 78 | 46 | 82 | 56 | 90 |
| ISQ-S | 4 | 7 | 29 | 82 | 48 | 85 | 57 | 88 |
| ISQ-S | 4 | 10 | 17 | 64 | 23 | 53 | 25 | 59 |
| ISQ-S | 7 | 2 | 15 | 48 | 20 | 48 | 27 | 60 |
| ISQ-S | 7 | 4 | 25 | 76 | 49 | 82 | 57 | 88 |
| ISQ-S | 7 | 7 | 32 | 79 | 45 | 82 | 53 | 87 |
| ISQ-S | 7 | 10 | 21 | 64 | 24 | 55 | 30 | 72 |
| ISQ-S | 10 | 2 | 20 | 60 | 30 | 65 | 37 | 72 |
| ISQ-S | 10 | 4 | 26 | 68 | 36 | 73 | 44 | 78 |
| ISQ-S | 10 | 7 | 24 | 64 | 31 | 70 | 40 | 76 |
| ISQ-S | 10 | 10 | 14 | 52 | 21 | 48 | 24 | 61 |
| PVDFP | 2 | 2 | 17 | 53 | 30 | 70 | 31 | 76 |
| PVDFP | 2 | 4 | 29 | 74 | 28 | 64 | 39 | 78 |
| PVDFP | 2 | 7 | 23 | 69 | 25 | 67 | 28 | 71 |
| PVDFP | 2 | 10 | 19 | 59 | 26 | 63 | 37 | 76 |
| PVDFP | 4 | 2 | 18 | 53 | 24 | 65 | 29 | 76 |
| PVDFP | 4 | 4 | 25 | 68 | 23 | 57 | 28 | 66 |
| PVDFP | 4 | 7 | 22 | 67 | 27 | 67 | 32 | 75 |
| PVDFP | 4 | 10 | 14 | 53 | 31 | 61 | 37 | 77 |
| PVDFP | 7 | 2 | 16 | 56 | 42 | 78 | 56 | 89 |
| PVDFP | 7 | 4 | 23 | 66 | 43 | 81 | 53 | 86 |
| PVDFP | 7 | 7 | 18 | 64 | 20 | 49 | 27 | 65 |
| PVDFP | 7 | 10 | 19 | 56 | 43 | 78 | 55 | 87 |
| PVDFP | 10 | 2 | 18 | 54 | 27 | 66 | 24 | 61 |
| PVDFP | 10 | 4 | 26 | 68 | 25 | 55 | 28 | 64 |
| PVDFP | 10 | 7 | 25 | 68 | 36 | 70 | 47 | 83 |
| PVDFP | 10 | 10 | 17 | 56 | 52 | 87 | 52 | 82 |
| PTFLH | 2 | 2 | 7 | 20 | 8 | 23 | 11 | 40 |
| PTFLH | 2 | 4 | 18 | 56 | 26 | 69 | 49 | 83 |
| PTFLH | 2 | 7 | 15 | 51 | 18 | 54 | 17 | 53 |
| PTFLH | 2 | 10 | 3 | 17 | 8 | 28 | 11 | 41 |
| PTFLH | 4 | 2 | 10 | 35 | 16 | 54 | 25 | 62 |
| PTFLH | 4 | 4 | 18 | 57 | 31 | 71 | 44 | 83 |
| PTFLH | 4 | 7 | 16 | 52 | 20 | 57 | 21 | 63 |
| PTFLH | 4 | 10 | 5 | 26 | 11 | 42 | 18 | 54 |
| PTFLH | 7 | 2 | 14 | 49 | 20 | 52 | 31 | 69 |
| PTFLH | 7 | 4 | 19 | 60 | 27 | 69 | 41 | 77 |
| PTFLH | 7 | 7 | 17 | 55 | 22 | 61 | 25 | 68 |
| PTFLH | 7 | 10 | 4 | 21 | 9 | 33 | 16 | 53 |
| PTFLH | 10 | 2 | 3 | 16 | 5 | 19 | 9 | 33 |
| PTFLH | 10 | 4 | 8 | 35 | 19 | 59 | 27 | 67 |
| PTFLH | 10 | 7 | 6 | 28 | 8 | 28 | 11 | 33 |
| PTFLH | 10 | 10 | 2 | 13 | 6 | 21 | 8 | 30 |

Any membrane reactors from Table 3 that were able to achieve at least 50% conversion after 4 h (third use at 70 degrees C.) were subjected to a total of 10 use cycles, two at 60 degrees C. and eight more at 70 degrees C. to monitor the stability of the membrane-immobilized catalyst Table 4.

TABLE 4

| | | | % conversion at 4 h, 70 deg C. | | | | | | | | | | |
|---|---|---|---|---|---|---|---|---|---|---|---|---|---|
| | pH | pH | use# | | | | | | | | | | % activity (use 10 |
| support | bind | wash | 1 | 2 | 3 | 4 | 5 | 6 | 7 | 8 | 9 | 10 | vs use 3) |
| K183 | 2 | 4 | 13 | 42 | 48 | 45 | 43 | 41 | 38 | 42 | 40 | 35 | 73 |
| K183 | 4 | 4 | 7 | 39 | 51 | 44 | 41 | 42 | 40 | 45 | 44 | 41 | 80 |
| K183 | 4 | 7 | 40 | 48 | 52 | 44 | 42 | 42 | 42 | 46 | 42 | 39 | 75 |
| K183 | 7 | 4 | 7 | 40 | 52 | 48 | 44 | 42 | 42 | 44 | 45 | 42 | 81 |
| K183 | 10 | 4 | 7 | 44 | 51 | 46 | 44 | 44 | 45 | 43 | 44 | 44 | 86 |
| PTF-LD | 2 | 4 | 24 | 40 | 51 | 47 | 42 | 42 | 42 | 43 | 42 | 42 | 82 |
| PTF-LD | 4 | 4 | 21 | 40 | 56 | 47 | 45 | 52 | 41 | 47 | 46 | 47 | 84 |
| PTF-LD | 7 | 4 | 22 | 39 | 57 | 49 | 49 | 44 | 43 | 47 | 48 | 42 | 74 |
| PVDF-P | 7 | 2 | 16 | 42 | 56 | 29 | 30 | 30 | 31 | 32 | 31 | 32 | 57 |
| PVDF-P | 7 | 4 | 23 | 43 | 53 | 55 | 53 | 60 | 58 | 60 | 48 | 44 | 83 |
| PVDF-P | 7 | 10 | 19 | 43 | 55 | 43 | 37 | 40 | 36 | 40 | 36 | 44 | 80 |
| PVDF-P | 10 | 10 | 17 | 52 | 52 | 44 | 46 | 45 | 39 | 44 | 43 | 39 | 75 |
| UV150 | 2 | 4 | 21 | 40 | 53 | 52 | 56 | 56 | 57 | 53 | 56 | 52 | 98 |
| UV150 | 2 | 7 | 29 | 43 | 52 | 42 | 51 | 50 | 53 | 54 | 53 | 51 | 98 |
| UV150 | 4 | 4 | 15 | 38 | 56 | 56 | 56 | 57 | 55 | 48 | 49 | 55 | 98 |
| UV150 | 4 | 7 | 23 | 37 | 54 | 48 | 49 | 49 | 45 | 44 | 45 | 44 | 81 |
| UV150 | 7 | 4 | 13 | 33 | 57 | 54 | 55 | 51 | 46 | 53 | 52 | 53 | 93 |
| UV150 | 10 | 4 | 8 | 33 | 55 | 50 | 52 | 50 | 54 | 54 | 51 | 50 | 91 |

Example 3

Strip and Re-Load Experiment

One of the proposed advantages of a membrane-immobilized enzyme catalyst is the potential to strip inactive catalyst from the membrane and re-immobilize the enzyme catalyst (e.g. fresh enzyme catalyst) to the stripped membrane. This was tested using a set of standards from Example 1. The 16 identical standard membrane reactors (Lipozyme CALB L immobilized on PVDF-M, bound and washed at pH7) were randomly divided into 4 treatment sets. The first set (untreated control) was used as is. The second set (stripped control) was subjected to a treatment to strip the enzyme from the membrane. The membrane was stripped at 70 deg C. with stirring with 12 ml of a 2 wt % solution of Triton X100 in water. The stripping step was performed twice for 30 minutes each. Then the stripped membrane was washed again with 12 ml water, twice at 70 deg C. then twice more at room temperature. A third set of standards (water re-load) was stripped as described, then reloaded with fresh enzyme catalyst as described in the standard protocol, but omitting the ethanol pre-wet step. The last set of standards (ethanol re-load) was reloaded with fresh enzyme catalyst according to the standard protocol, including the ethanol pre-wetting step. The membrane reactors were then tested for activity using the EHP activity assay as in Example 1.

The results of the re-load experiment are included in Table 5. According to the results of the activity assay, by the fourth use, this set of membrane reactors was already beginning to exhibit a loss of activity (Treatment group 1 vs. 2). Upon detergent treatment, the enzyme was stripped from the membrane (2 vs. 3), although the stripping procedure did not completely remove the enzyme, as there was a small but significant amount of activity left on the stripped membrane (3 vs. 6). The best conditions for re-binding active enzyme included an ethanol pre-wetting step (4 vs. 5), as in the original protocol. The rate of conversion to product with the re-loaded enzyme (including an ethanol pre-wetting) was not significantly different from the initial activity of the membrane reactor (5 vs. 1).

Table 5. Enzyme activity, measured as rate of Ethylhexyl palmitate (EHP) formation, of lipase bound to Millipore Immobilon-P PVDF membrane at pH 7 and equilibrated at pH 7 (treatment 1, 2), after detergent stripping (3) and re-binding fresh enzyme to the stripped membranes (4, 5). Conversion rates at 4 h marked with the same bold lower-case letter are not significantly different from each other.

TABLE 5

| Treatment group | Description (number of replicates) | % Conversion to EHP at 60 deg C. Avg (std dev) | |
|---|---|---|---|
| | | After 4 h | After 24 h |
| 1 | Experimental standards; initial use (n = 16) | 27 (2.3) a | 73 (2.4) |
| 2 | Untreated controls; fourth use (n = 4) | 21 (2.9) b | 57 (5.8) |
| 3 | Stripped membranes (n = 4) | 3 (0) c | 17 (1.5) |
| 4 | Re-loaded with enzyme; water wet (n = 4) | 13 (4.6) d | 51 (11.2) |
| 5 | Re-loaded with enzyme; ethanol pre-wet (n = 4) | 25 (3.1) a, b | 71 (4.4) |
| 6 | No enzyme, no membrane (n = 3) | 2 (0) | 10 (0.6) |

Example 4

Effect of Support Pore Size and Immobilization Temperature on Enzyme Activity

An enzyme stock solution (Lipozyme CALB L) was immobilized on three different Microdyne Nadir fluoropolymer supports, with different pore sizes, using the Standard Protocol as described in Example 1. In each case, the effective pore size of the membrane exceeded the size of the enzyme catalyst. The temperature at which the immobilization occurred was varied, using either 4 deg C. or 22 deg C. Activity of the supported catalysts was evaluated with the Ethylhexyl palmitate reaction, described in Example 1. The results of the activity tests are summarized in Table 6. (nd=no data)

TABLE 6

| Membrane | pH bind | pH wash | immobilization temp (degrees C.) | Use #1, 60 deg C. | | Use #2, 60 deg C. | | Use #3, 70 deg C. | |
|---|---|---|---|---|---|---|---|---|---|
| | | | | % EHP 4 h | % EHP 24 h | % EHP 4 h | % EHP 24 h | % EHP 4 h | % EHP 24 h |
| MV020 | 2 | 4 | 4 | 5 | 39 | nd | nd | 41 | 79 |
| MV020 | 2 | 4 | 22 | 4 | 31 | nd | nd | 46 | 80 |
| MV020 | 4 | 4 | 4 | 4 | 23 | nd | nd | 48 | 72 |
| MV020 | 4 | 4 | 22 | 3 | 17 | nd | nd | 41 | 77 |
| MV020 | 7 | 4 | 4 | 11 | 45 | nd | nd | 44 | 85 |
| MV020 | 7 | 4 | 22 | 8 | 40 | nd | nd | 43 | 79 |
| UV150 | 2 | 4 | 4 | 23 | 74 | nd | nd | 59 | 93 |
| UV150 | 2 | 4 | 22 | 17 | 70 | nd | nd | 61 | 93 |
| UV150 | 4 | 4 | 4 | 14 | 68 | nd | nd | 60 | 93 |
| UV150 | 4 | 4 | 22 | 21 | 76 | nd | nd | 61 | 95 |
| UV150 | 7 | 4 | 4 | 11 | 54 | nd | nd | 59 | 93 |
| UV150 | 7 | 4 | 22 | 14 | 57 | nd | nd | 61 | 91 |
| UV200 | 2 | 4 | 4 | 8 | 60 | nd | nd | 54 | 91 |
| UV200 | 2 | 4 | 22 | 12 | 68 | nd | nd | 54 | 91 |
| UV200 | 4 | 4 | 4 | 12 | 56 | nd | nd | 58 | 94 |
| UV200 | 4 | 4 | 22 | 5 | 50 | nd | nd | 58 | 94 |
| UV200 | 7 | 4 | 4 | 14 | 58 | nd | nd | 61 | 94 |
| UV200 | 7 | 4 | 22 | 11 | 54 | nd | nd | 58 | 93 |

Example 5

Effect of Binding and Washing Solution

An enzyme stock solution (Lipozyme CALB L) was immobilized on five different fluoropolymer supports using the Standard Protocol. Unbuffered water was used as the binding solution, and either water or pH 4 buffer (Hydrion) was used as the wash solution. The 24 hour immobilization was performed at 22 deg C. Activity of the supported catalysts was evaluated with the Ethylhexyl palmitate reaction, described in Example 1. The results of the activity tests are summarized in Table 7.

Example 6

Enzyme Stock Solution from *Candida antarctica* Lipase B Lyophilized Powder, Effect of Surfactant An enzyme stock solution was made by reconstituting a lyophilized preparation of *Candida antarctica* lipase B in water, in the absence or presence of added surfactant. The lyophilized enzyme preparation was a product of c-LEcta GmbH, Deutscher Platz 5, 04103 Leipzig, Germany, and contained approximately 2.7 wt % protein, according to a Bradford assay. The nonionic surfactant Tween 20 was optionally added to the enzyme stock solution at 10 mg/ml.

TABLE 7

| Membrane | Wash solution | Use #1, 60 deg C. | | Use #2, 60 deg C. | | Use #3, 70 deg C. | |
|---|---|---|---|---|---|---|---|
| | | % EHP 4 h | % EHP 24 h | % EHP 4 h | % EHP 24 h | % EHP 4 h | % EHP 4 h |
| PVDF-M | water | 28 | 82 | 58 | 90 | 46 | 86 |
| K180 | water | 5 | 60 | 35 | 78 | 39 | 82 |
| UV150 | water | 25 | 78 | 50 | 93 | 57 | 94 |
| UV200 | water | 10 | 59 | 33 | 77 | 44 | 81 |
| PTF-LD | water | 23 | 72 | 38 | 80 | 43 | 83 |
| PVDF-M | pH 4 | 32 | 79 | 52 | 95 | 57 | 95 |
| K180 | pH 4 | 12 | 66 | 35 | 81 | 53 | 92 |
| UV150 | pH 4 | 21 | 76 | 52 | 91 | 59 | 94 |
| UV200 | pH 4 | 10 | 71 | 49 | 91 | 58 | 95 |
| PTF-LD | pH 4 | 24 | 72 | 40 | 81 | 48 | 91 |

The enzyme stock solutions were immobilized on Millipore Immobilon P (PVDF-M), using the Standard Protocol, except that unbuffered water was used as both the binding and washing solution, and the 24 h immobilization was carried out at 22 deg C. The activity of the fluoropolymer-supported catalyst was determined using the standard ethylhexyl palmitate reaction, including re-using the biocatalyst system. Table 8 summarizes the results of the activity assay.

TABLE 8

| Candida antarctica lipase B Enzyme stock solution (mg/ml) | | | Use #1, 60 deg C. | | Use #2, 60 deg C. | | Use #3, 70 deg C. | |
|---|---|---|---|---|---|---|---|---|
| Powder | Protein | Tween 20 | % EHP 4 h | % EHP 24 h | % EHP 4 h | % EHP 24 h | % EHP 4 h | % EHP 24 h |
| 16 | 0.044 | 0 | 14 | 62 | 41 | 75 | 39 | 79 |
| 32 | 0.088 | 0 | 18 | 72 | 46 | 83 | 48 | 89 |
| 64 | 0.175 | 0 | 22 | 74 | 58 | 97 | 48 | 86 |
| 16 | 0.044 | 10 | 8 | 41 | 22 | 63 | 31 | 69 |
| 32 | 0.088 | 10 | 12 | 54 | 37 | 79 | 40 | 91 |
| 64 | 0.175 | 10 | 25 | 78 | 60 | 94 | 45 | 87 |

Example 7

Enzyme Stock Solution from *Thermomyces lanuginosus* Lyophilized Powder, Effect of Surfactant An enzyme stock solution was made by reconstituting a lyophilized preparation of *Thermomyces lanuginosus* lipase in water, in the absence or presence of added surfactant. The lyophilized enzyme preparation was a product of BioCatalytics, and contained approximately 2.5 wt % protein, according to a Bradford assay. The nonionic surfactants Pluronic L35, L61 or 10R5 were optionally added to the enzyme stock solution at 5 mg/ml. The enzyme stock solutions were immobilized on Millipore Immobilon P (PVDF-M), using the Standard Protocol, except that unbuffered water was used as both the binding and washing solution. The 24 h immobilization was carried out at 4 deg C. The activity of the fluoropolymer-supported catalyst was determined using the standard ethylhexyl palmitate reaction, including re-using the biocatalyst system. Table 9 summarizes the results of the activity assay.

TABLE 9

| Thermomyces lanuginosus Enzyme stock solution | | | Use #1, 60 deg C. | | Use #2, 60 deg C. | | Use #3, 70 deg C. | |
|---|---|---|---|---|---|---|---|---|
| Powder mg/ml | Protein mg/ml | Surfactant 5 mg/ml | % EHP 4 h | % EHP 24 h | % EHP 4 h | % EHP 24 h | % EHP 4 h | % EHP 24 h |
| 50 | 0.12 | L35 | 14 | 57 | 19 | 72 | 16 | 44 |
| 50 | 0.12 | L61 | 2 | 11 | 3 | 13 | 8 | 22 |
| 50 | 0.12 | 10R5 | 15 | 65 | 20 | 65 | 13 | 38 |
| 50 | 0.12 | none | 21 | 77 | 27 | 79 | 16 | 47 |

Example 8

Enzyme Stock Solution of *Candida antarctica* Lipase a on Fluoropolymer Support with Backing An enzyme stock solution (Novozyme 735, a solution of *Candida antarctica* lipase A) was immobilized on Microdyne Nadir fluoropolymer supports (UV150 and UV200), using the Standard Protocol, except that the volume of enzyme stock solution was 0.25 ml. Unbuffered water was used as the binding and washing solution. The 24 h immobilization was carried out at 22 deg C. The activity of the fluoropolymer-supported catalyst was determined using the standard lipase reaction, including re-using the biocatalyst system. Table 10 summarizes the results of the activity assay.

TABLE 10

| Membrane | Enzyme stock solution (ml) | Wash solution | Use #1, 60 deg C. | | Use #2, 60 deg C. | | Use #3, 70 deg C. | |
|---|---|---|---|---|---|---|---|---|
| | | | % EHP 4 h | % EHP 24 h | % EHP 4 h | % EHP 24 h | % EHP 24 h | % EHP 4 h |
| UV150 | 0.25 | water | 63 | 93 | 75 | 93 | 82 | 92 |
| UV200 | 0.25 | water | 51 | 96 | 80 | 97 | 85 | 94 |

Example 9

Enzyme Stock Solution of *Candida antarctica* Lipase a on Fluoropolymer Support without Backing An enzyme stock solution (Novozyme 735, a solution of *Candida antarctica* lipase A) was immobilized on Millipore Immobilon P (PVDF-M), using the Standard Protocol, except that the volume of enzyme stock solution was varied. Unbuffered water was used as the binding solution and either water or pH4 buffer (Hydrion) was used as the washing solution. The 24 h immobilization was carried out at 22 deg C. The activity of the fluoropolymer-supported catalyst was determined using the standard ethylhexyl palmitate reaction, including re-using the biocatalyst system. Table 11 summarizes the results of the activity assay.

TABLE 11

| Membrane | Enzyme stock solution (ml) | Wash solution | Use #1, 60 deg C. | | Use #2, 60 deg C. | | Use #3, 70 deg C. | |
|---|---|---|---|---|---|---|---|---|
| | | | % EHP 4 h | % EHP 24 h | % EHP 4 h | % EHP 24 h | % EHP 4 h | % EHP 24 h |
| PVDF-M | 0.25 | water | 78 | 92 | 80 | 94 | 80 | 92 |
| PVDF-M | 0.5 | water | 86 | 95 | nd | nd | nd | nd |
| PVDF-M | 1 | water | 81 | 94 | 78 | 94 | 76 | nd |
| PVDF-M | 2 | water | 81 | 94 | 80 | 94 | nd | nd |
| PVDF-M | 0.25 | pH 4 | 78 | 94 | 79 | 96 | 52 | nd |
| PVDF-M | 0.5 | pH 4 | 79 | 94 | 83 | 95 | 68 | nd |
| PVDF-M | 1 | pH 4 | 81 | 94 | 80 | 96 | 61 | nd |
| PVDF-M | 2 | pH 4 | 81 | 94 | 79 | 96 | nd | nd |

Having described the invention in detail, those skilled in the art will appreciate that modifications may be made to the various aspects of the invention without departing from the scope and spirit of the invention disclosed and described herein. It is, therefore, not intended that the scope of the invention be limited to the specific embodiments illustrated and described but rather it is intended that the scope of the present invention be determined by the appended claims and their equivalents. Moreover, all patents, patent applications, publications, and literature references presented herein are incorporated by reference in their entirety for any disclosure pertinent to the practice of this invention.

What is claimed is:

1. An immobilized catalyst comprising a porous fluoropolymer support having at least one layer and at least one enzyme catalyst immobilized via non-covalently binding the enzyme catalyst to the support,
   wherein the support is selected from the group consisting of a membrane, a film, a tape, a fiber, a hollow fiber, a tube, a braid, and a sponge,
   the effective pore size of each layer of the support is greater than the size of the enzyme catalyst, and
   the immobilized catalyst maintains catalytic activity for between 2 and 50 reuses, and
wherein the enzyme catalyst is selected from the group consisting of hydrolytic enzyme, transferase, isomerase, ligase, dehydratase, catalase, hydroxylase, nitrilase, nuclease, polymerase, kinase, phosphatase and mixtures thereof.

2. The catalyst according to claim 1, wherein the enzyme catalyst is in the form of an isolated enzyme, a mixture of enzymes, a cell extract, or a whole cell.

3. A reactor comprising the immobilized catalyst according to claim 1.

4. The reactor according to claim 3, wherein the reactor comprises a cartridge wherein the cartridge comprises the immobilized catalyst.

5. An immobilized catalyst comprising a porous fluoropolymer membrane and at least one catalyst immobilized via non-covalently binding the enzyme catalyst to the membrane,
   wherein the enzyme catalyst is immobilized on both surfaces of the membrane; and
   the effective pore size of each layer of the membrane is greater than the size of the enzyme catalyst, and
   the immobilized catalyst maintains catalytic activity for between 2 and 50 reuses, and
wherein the enzyme catalyst is selected from the group consisting of hydrolytic enzyme, transferase, isomerase, ligase, dehydratase, catalase, hydroxylase, nitrilase, nuclease, polymerase, kinase, phosphatase and mixtures thereof.

6. The catalyst according to claim 5, wherein the membrane is symmetrical.

7. The catalyst according to claim 5, wherein the membrane is hydrophobic.

8. The catalyst according to claim 5, wherein the membrane has a single layer.

9. The catalyst according to claim 5, wherein the enzyme catalyst is in the form of an isolated enzyme, a mixture of enzymes, a cell extract, or a whole cell.

10. A cartridge comprising the immobilized catalyst according to claim 5.

11. A reactor comprising the cartridge according to claim 10.

12. A method of producing an immobilized catalyst comprising contacting at least one enzyme catalyst and the support,
   wherein the support has at least one layer and is selected from the group consisting of a membrane, a film, a tape, a fiber, a hollow fiber, a tube, a braid, and a sponge;
   wherein the enzyme catalyst is immobilized via non-covalently binding the enzyme catalyst to the support; and
   the effective pore size of each layer of the support is greater than the size of the enzyme catalyst, and
   the immobilized catalyst maintains catalytic activity for between 2 and 50 reuses, and
wherein the enzyme catalyst is selected from the group consisting of hydrolytic enzyme, transferase, isomerase, ligase, dehydratase, catalase, hydroxylase, nitrilase, nuclease, polymerase, kinase, phosphatase and mixtures thereof.

13. The method according to claim 12 further comprising:
   stripping the enzyme catalyst from the fluoropolymer support to remove any enzyme catalyst bound to the support, and contacting the fluoropolymer support with at least one enzyme catalyst.

14. The method according to claim 12, further comprising pre-wetting the support with a pre-wetting agent selected from the group consisting of water, an alcohol, a polyol, and a combination thereof.

15. The method according to claim 14, wherein the pre-wetting agent is removed from the support prior to contacting the support with the enzyme catalyst.

16. The method according to claim 12, wherein the enzyme catalyst is in the form of an isolated enzyme, a mixture of enzymes, a cell extract, or a whole cell.

17. The method according to claim 12, wherein the contacting is from about 0.5 hours to about 144 hours.

18. The method according to claim 17, wherein the contacting is from about 2 hours to about 48 hours.

19. The method according to claim 12, wherein the contacting is at a temperature of from about 0° C. to about 100° C.

20. The method according to claim 19, wherein the contacting is at a temperature of from about 4° C. to about 80° C.

21. The method according to claim 20, wherein the contacting is at a temperature of from about 15° C. to about 50° C.

22. A method of producing a chemical comprising contacting at least one reactant with at least one immobilized catalyst to produce the chemical, wherein the enzyme catalyst is immobilized via non-covalently binding the enzyme catalyst on a porous fluoropolymer support;

the support has at least one layer and is selected from the group consisting of membrane, a film, a tape, a fiber, a hollow fiber, a tube, a braid, and a sponge; and the effective pore size of each layer of the support is greater than the size of the enzyme catalyst, and the immobilized catalyst maintains catalytic activity for between 2 and 50 reuses, and wherein the enzyme catalyst is selected from the group consisting of hydrolytic enzyme, transferase, isomerase, ligase, dehydratase, catalase, hydroxylase, nitrilase, nuclease, polymerase, kinase, phosphatase and mixtures thereof.

23. The method according to claim 22, wherein the catalyst is in the form of an isolated enzyme, a mixture of enzymes, a cell extract, or a whole cell.

* * * * *